United States Patent [19]

Luceri et al.

[11] Patent Number: 5,135,521
[45] Date of Patent: Aug. 4, 1992

[54] SANITARY NAPKIN WITH COMPOSITE COVER

[75] Inventors: Thomas J. Luceri, Bridgewater; Deborah J. Parr, Plainsboro, both of N.J.

[73] Assignee: McNeil-PPC, Inc., Milltown, N.J.

[21] Appl. No.: 464,808

[22] Filed: Jan. 16, 1990

Related U.S. Application Data

[63] Continuation of Ser. No. 387,673, Jul. 31, 1989, abandoned, which is a continuation of Ser. No. 158,415, Feb. 22, 1988, abandoned, which is a continuation of Ser. No. 886,271, Jul. 15, 1986, abandoned.

[51] Int. Cl.$^5$ ............................................. A61F 13/15
[52] U.S. Cl. ................................. 604/383; 604/370; 428/137
[58] Field of Search ............... 604/369, 372, 375, 378, 604/383, 384, 385.1, 370, 371; 428/137

[56] References Cited

U.S. PATENT DOCUMENTS

| | | | |
|---|---|---|---|
| 4,324,246 | 4/1982 | Mullane et al. | 604/370 X |
| 4,397,644 | 8/1983 | Matthews et al. | 604/378 |
| 4,690,679 | 9/1987 | Mattingly et al. | 604/383 |
| 4,820,295 | 4/1989 | Chapas et al. | 604/385.1 |
| 4,846,813 | 7/1989 | Raley | 604/385.1 |
| 4,883,707 | 11/1989 | Newkirk | 604/372 |
| 5,019,062 | 5/1991 | Ryan et al. | 604/383 |

FOREIGN PATENT DOCUMENTS 165807 12/1985 European Pat. Off. .

Primary Examiner—C. Fred Rosenbaum
Assistant Examiner—Mark O. Polutta

[57] ABSTRACT

A cover for a sanitary napkin or other absorbent product is provided which includes an outer layer of a hydrophobic material. The outer layer contains fluid passageways which are small enough so that the outer layer alone will not pass liquid therethrough. A second, liner layer is bonded to the interior surface of the outer layer and is comprised of a nonwoven web which is at least slightly wettable so as to draw liquids through the passageways of the outer layer. The liner layer contains large capillaries so that at least a majority of the liquid entering the liner layer from the fluid passageways will pass through the liner to the absorbent core of the product.

19 Claims, 4 Drawing Sheets

SANITARY NAPKIN WITH COMPOSITE COVER

This is a continuation of application Ser. No. 387,673, filed Jul. 31, 1989 abandoned which in turn was a continuation of Ser. No. 158,415 filed Feb. 22, 1988, abandoned which in turn was a continuation of Ser. No. 06/886,271 filed Jul. 15, 1986 abandoned.

This invention relates to absorbent products such as diapers, sanitary napkins, wound dressings and the like and, in particular, to such products having a composite cover material which is intended to transmit fluids to an absorbent core.

In general, such products have an absorbent core comprising one or more layers of fluid absorbent material such as wood pulp, rayon, gauze, tissue or the like, and in some cases synthetic hydrophilic material such as hydrophilic polyurethane foam may be used. The hydrophilic material is generally provided in the form of a pad, which may have a rectangular or somewhat oval shape. To protect the clothing of the user from being stained or wetted by the body fluids absorbed by the hydrophilic material, the pad is generally backed by a body fluid impervious barrier sheet. The absorbent product is positioned on the body with the hydrophilic material facing the body and the fluid impervious barrier facing the clothing of the user.

To enhance the sense of comfort for the user, absorbent products also generally employ a cover material or facing which covers the body-facing surface of the hydrophilic material. The purpose of the cover is to structurally contain the loosely packed absorbent material and to protect the body from direct contact with the absorbent pad. The cover is pervious to body fluids on the side of the product that is placed against the body, and is preferably relatively nonabsorbent so as to promote the transfer of body fluids to the absorbent pad with minimal fluid retention by the cover. The fluid pervious characteristic may be obtained by use of an apertured film or nonwoven cover, for instance. A well-designed cover will thus remain relatively dry in use, thereby increasing the comfort of the user.

The comfort of the user is further enhanced if the cover, in addition to its properties of high fluid transmissivity and minimal fluid retention, exhibits the characteristic of unidirectional fluid transmissivity. This will improve what is known as the rewet characteristic of the absorbent product. As previously mentioned, the cover should quickly and easily transmit fluid through the absorbent core. But as the core becomes saturated, fluid will tend to pass back through the cover, or rewet, causing user discomfort. To a significant extent, rewetting may be inhibited by designing the absorbent core so that fluid retention in the core is greatest in a region of the core that is most remote from the cover. For instance, the absorbent core may be formed of a composite of different material layers with a superabsorbent located in the layer which opposes the fluid impervious barrier. The layer opposing the cover is composed of a material with lesser absorbent characteristics. Such an absorbent core construction will establish a gradient of fluid retentivity, whereby fluid will preferentially tend to be retained in the superabsorbent layer most remote from the cover.

As the absorbent core becomes increasingly saturated during use or is subjected to a pressure, there will be a tendency of the fluid to retransmit back through the cover, or rewet the cover's surface and hence the body of the user. The discomfort caused by rewetting can impel the user to discard the absorbent product before its useful life has terminated. To inhibit such rewetting and resultant user discomfort, it is desirable for the cover to resist passage of fluid through from the absorbent core to the cover's surface. A cover which readily transmits fluid from its body-facing surface to the absorbent core, but resists the transmission of fluid in the reverse direction, is characterized herein as exhibiting a desirable unidirectional fluid transmissivity characteristic.

In accordance with the principles of the present invention an absorbent product is described which provides enhanced user comfort. The inventive absorbent product includes a fluid impervious barrier, an absorbent core, and a body-facing composite cover. The composite cover comprises an outer, body-facing layer of substantially hydrophobic material having fluid passageways passing through the layer. The passageways are small enough so that fluid, when deposited on the absorbent core facing surface of the layer, will not pass through the layer. The composite cover further includes an inner, absorbent core facing layer of a nonwoven fabric comprised of materials which have some minimal degree of wettability. The inner layer is bonded to the outer layer such that the wettable material is proximately located at the fluid passageway openings (at the absorbent core facing surface) of the outer layer. The wettable material will then draw fluids through the passageways and into the inner layer. The inner layer has a capillary structure that is insufficient to retain a majority of the fluid within the inner layer, so that a majority of the fluid will pass through the inner layer under the influence of gravity under the test conditions described herein, with insubstantial fluid wicking. A composite cover with these properties exhibits the desirable unidirectional fluid transmissivity characteristic as shown by the tests described herein, which are designed to emphasize this characteristic.

Figure 1:
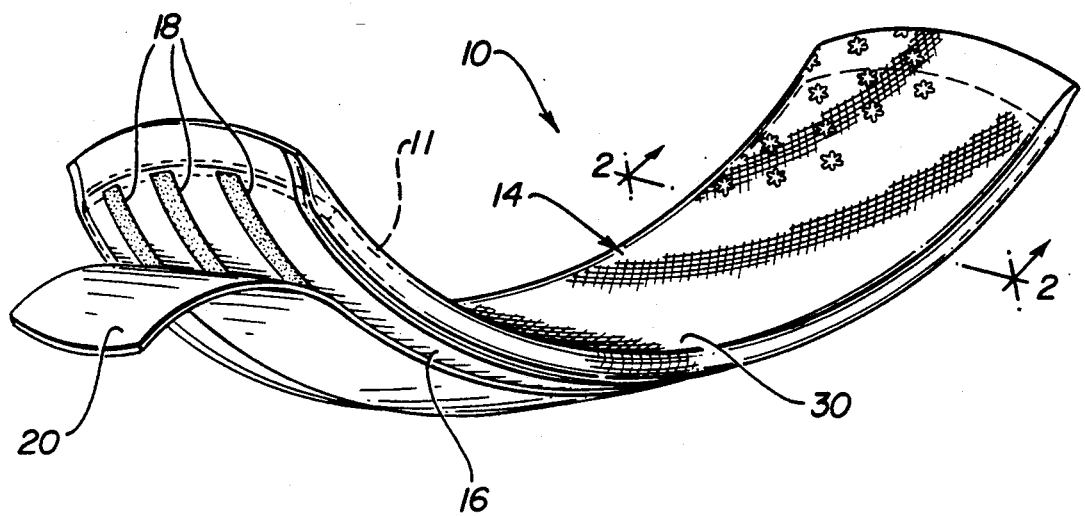
FIG. 1 illustrates a sanitary napkin constructed in accordance with the principles of the present invention.
Figure 2:
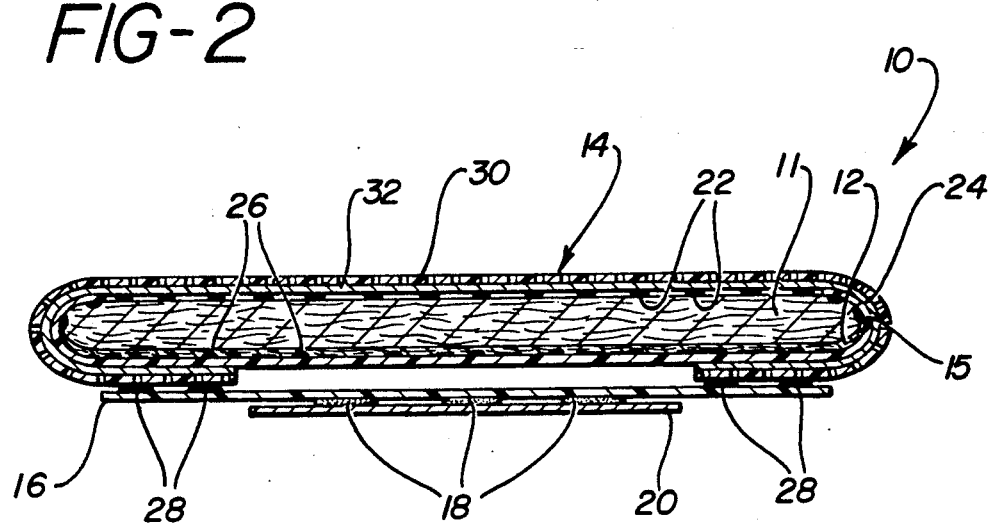
FIG. 2 is a cross-sectional view of the napkin of FIG. 1.

Referring concurrently to FIGS. 1 and 2, a sanitary napkin 10 constructed in accordance with the principles of the present invention is shown. The napkin 10 has a generally rectangular shape. The napkin may exhibit an alternative shape, such as an hourglass shape. Body fluids are absorbed and retained by an absorbent core 15, shown in FIG. 2, which is sealed between a composite cover 14 and a fluid impervious barrier 16. The absorbent core 15 may be comprised of any of the well-known absorbents such as wood pulp, rayon, synthetic absorbents in the form of fibers, powder, or foam or combinations thereof. Absorbency enhancers such as the so-called "super absorbent" materials may be employed. Non-hydrophilic materials may also be employed in combination with absorbent materials. One such example is low density, thermal bonded nonwoven fabric comprising a mixture of absorbent fibers and staple length conjugate fibers. The absorbent fibers may be wood pulp or other cellulosic fibers which may have been treated to enhance absorbency. Suitable conjugate fibers are fibers which comprise a polyester core surrounded by a sheath of polyethylene. A highly satisfactory absorbent pad is produced by a thermally bonded absorbent fabric comprising 54% by weight of wood pulp fibers and 46% by weight of conjugate fibers having a staple length of 3.81 cm. and a denier of 3.0. The fabric is stabilized by passing hot air through the fibers and thereby melting the polyethylene which bonds the fibers together upon cooling. Such a fabric is capable of holding about 17 times its own weight of distilled water. Alternatively, an absorbent core of densified web material may be employed, as described in U.S. Pat. No. 4,551,142.

In the preferred embodiment of FIG. 2 the absorbent core is a composite of two pads or layers 11 and 12. The top layer 11 adjacent the composite cover 14 consists of low density wood pulp fluff, and is adhered to the cover 14 with an emulsion adhesive 22. The bottom layer 12 is a homogeneous blend of pulp fluff and a superabsorbent which are calendered by heat and pressure to form a highly densified layer. The two layers 11, 12 are wrapped in and adhered to a polyethylene "boat" 24 using an emulsion adhesive 26. The purpose of the low density fluff layer 11 is to rapidly absorb fluids and to provide the desired product thickness. The purpose of the high density wood pulp/superabsorbent layer 12 is to draw fluid to the bottom of the product remote from the cover, rapidly distribute the fluid throughout the layer 12, and retain the fluid under pressure. Additionally this layer 12 provides desired product stability. The purpose of the polyethylene boat 24 is fluid containment, whereby fluid will not be transferred from the bottom and sides of the absorbent pad to an outer location where it could stain the undergarments of the user.

In the preferred embodiment the top layer 11 consists of from 1.5 to 4.0 grams of conventional low density ground wood pulp fluff. The bottom layer 12 consists of from 1.5 to 4.0 grams of ground wood pulp fluff and from 0.3 to 0.71 grams of the superabsorbent Sanwet 1M-1000, produced by Sanyo Chemical Industries, Ltd. of Kyoto, Japan. The polyethylene boat 24 consists of a 0.5 mil polyethylene film, and the emulsion adhesive used at 22 and 26 is Fuller L-3585-U emulsion adhesive produced by the H. B. Fuller Co. of Minneapolis, Minn.

The fluid impervious barrier 16 acts as a further barrier to body fluids to prevent staining of the undergarments of the user, and also provides a backing for adhesive mean which permits the adhesively anchored product to be removed from a user's undergarment without tearing. The barrier may comprise any thin flexible body fluid impermeable material such as a polymeric film, e.g., polyethylene, polypropylene, or cellophane. Alternatively, the barrier may comprise a normally fluid pervious material that has been treated to be impervious such as impregnated fluid repellant paper or a repellant treated microdenier material. In the preferred embodiment of FIG. 2, the cover 14 forms a C-shaped wrap around the top and sides of the polyethylene boat and absorbent core, and is folded a short distance under the bottom of the boat 24 on each side of the napkin. The barrier 16 is adhesively affixed to both sides of the cover by Fuller HN-6680 hot melt adhesive as shown at 28 to form the garment facing side of the napkin. In the preferred embodiment the barrier 16 comprises a sheet of 1.5 mil embossed polyethylene.

Disposed on the garment facing surface of the barrier 16 are longitudinally extending pressure-sensitive adhesive means 18, provided for attaching the napkin to the crotch portion of an undergarment. While such adhesive means are illustrated in the form of longitudinally extending lines, it will be understood that various patterns such as spots or transverse lines are suitable. The adhesive employed may be any of the large number of pressure-sensitive adhesives that are commercially available, including water based adhesives such as acrylate adhesives, e.g., vinyl acetate/2-ethylhexyl acrylate copolymer which may be combined with tackifiers. Alternatively, the adhesive may also comprise a pressure sensitive rapid-setting hot melt adhesive. The adhesive element may also comprise a double faced tape.

It may be appreciated that an alternative construction would be to dispose the adhesive means 18 directly on the garment facing surface of the polyethylene boat, dispensing with the need for the barrier 16. In such an arrangement the cover 14 would then be sealed to the boat material where the cover overlies the boat. The boat would then be constructed from a fluid impervious material that is strong enough to resist tearing when the napkin is removed from the user's undergarment after use.

Overlying the adhesive means 18 is a protective release strip 29 which is provided to protect the adhesive means from dirt and unintended adhesion prior to use. The release strip 20 may be constructed of any suitable sheet-like material which adheres with sufficient tenacity to the adhesive means to remain to remain in place prior to use but which can be readily removed when the napkin is to be used. A particularly useful material is a semibleached kraft paper, the adhesive contacting side of which has been silicone treated to provide easy release from the adhesive means 18.

In accordance with the principles of the present invention, the cover 14 of the napkin 10 is a composite of two layers, an outer, body-facing layer 30 and an inner, pad-facing layer or liner 32. The two layers are bonded or laminated together so that the body-facing surface of the liner is in intimate contact with the pad-facing side of the outer layer 30.

The outer layer 30 comprises a sheet of hydrophobic material having apertures or passageways for fluid to pass therethrough. It may be formed of any suitable porous, hydrophobic material, such as a nonwoven or an apertured film sheet, foam material, or a hydrophilic material such as rayon which has been treated to be hydrophobic. The fluid apertures or passageways in the outer layer are small enough so that when a fluid is deposited on the pad-facing surface of the layer in accordance with the test described below, the fluid does not pass through the sheet.

The liner or insert 32 is a nonwoven fabric which is comprised of materials, e.g., fibers, which have some minimal degree of wettability such that contact of the wettable material by liquid located in the fluid passageways of the outer layer causes the liquid to be drawn through the outer layer. For example, when the preferred liner containing wettable fibers is bonded to the outer layer, such fibers will be located immediately below the fluid passageways of the outer layer 30. When a fluid droplet is located on the body-facing side of the outer layer with the surface of the droplet extending into an aperture or passageway under the force of gravity or pressure, the surface of the droplet will contact one of the wettable fibers of the liner. This contact will cause the fluid droplet to be drawn through the outer layer and into the liner 32.

Further, the capillaries of the liner are large enough on average so that the liner itself will retain no more than a small amount of liquid, and will pass a majority of the liquid through to the underlying absorbent pad. In particular, the capillary forces within the liner, on average, must be overcome by the gravitational force acting on fluid droplets within the liner under the test conditions described below. The liner is thus characterized by having capillaries which on average are large enough to permit the ready passage of fluids from the outer layer to the absorbent pad with only slight wicking. In this way the liner will rapidly conduct fluid from the outer layer to the absorbent pad with insubstantial fluid wicking, thereby providing enhanced rewet characteristics of the absorbent product.

In the preferred embodiment the outer layer 30 comprises a coextruded, apertured film including a top or outer surface consisting primarily of linear low density polyethylene and a bottom or inner surface consisting primarily of ethylene vinyl acetate. This coextruded apertured film is most preferred for its ability to be heat sealed while retaining its apertured integrity, as described in U.S. patent application No. 840,290, filed Mar. 14, 1986 now U.S. Pat. No. 4,690,679 and entitled "COEXTRUDED APERTURED FILM SANITARY NAPKIN COVER". This coextruded apertured film is thermally bonded to the liner by melting the liner-facing ethylene vinyl acetate layer, while the unmelted linear low density polyethylene layer maintains film integrity. Since this apertured film is composed of hydrophobic materials, it is also desirable for its non-staining, dry appearing attributes. The preferred material has a basis weight of 1.0 oz./yd.$^2$, and exhibits a tensile strength in the machine direction of 3 lbs./3 inch width minimum and in the cross direction a 1 lb./3 inch width minimum. The open area ranges between 35% to 45%, with the apertures exhibiting an equivalent hydraulic diameter between 15 mils and 22 mils. The apertures have an average center-to-center spacing of about 0.028 inches. The apertured film has a thickness of approximately 0.004 inches as measured with a model 35B-30 Federal gauge.

The nonwoven insert 32 in the preferred embodiment is a blend of 75% bicomponent fusible fibers and 25% rayon fibers. The bicomponent fusible fiber is available from the American Enka Co. of Enka, North Carolina and is constructed with a core of polyester and a sheath of high density polyethylene. The ability of the sheath to melt during thermal bonding gives the liner a heat fusible characteristic. The fusible fiber has a denier of 3.0 and a staple length of 1.5 inches. The rayon fibers, available as type SN913 from Avtex Fibers, Inc. of Front Royal, Va. have a denier of 1.5 and a staple length of 1.25 inches. When the liner is thermally bonded to the apertured film by the fusible characteristic of the bicomponent fibers the wettable quality of the rayon fibers will draw fluids through the apertures of the film to be transported through the liner and absorbed by the the absorbent low density pulp fluff layer below. The insert 32 in the preferred embodiment has a basis weight of 0.8 oz./yd.$^2$, an overall thickness of about 15 mils, and a minimum dry tensile strength of 3 lbs./inch width in the machine direction and 0.4 lbs/inch width in the cross direction.

Other suitable materials for the insert include polyester and a foam material which is minimally wettable.

The preferred nonwoven insert is formed by thoroughly blending a mixture of the two fiber materials in the desired ratio. A carding process is used to form a high loft fiber web. The web is passed between two opposing mesh belts, one with a relatively fine mesh and the other with a relatively coarse mesh. The opposing mesh belts exert a pressure on the web which, together with other process parameters, gives the web its desired thickness. As the web passes between the belts, hot air is drawn through the mesh belts and the web. The air is heated to a temperature greater than the melting point of the polyethylene sheath of the bicomponent fibers, but less than the melting point of the polyester core of the fibers. This causes the bicomponent sheaths to melt and thermally bond the web into an integral liner layer. This technique also produces a fine mesh fabric veneer on the fine mesh side of the liner and a coarse mesh fabric veneer on the coarse mesh facing side of the liner, thereby providing a capillary gradient through the thickness of the liner. The coarse veneer surface is bonded directly to the apertured film so that the fine veneer surface will oppose the absorbent core. Thus the preferred liner has a favorable large-to-small capillary gradient to more readily conduct fluid from the fluid passageways of the film to the even finer capillary structure of the absorbent core.

Figure 3:
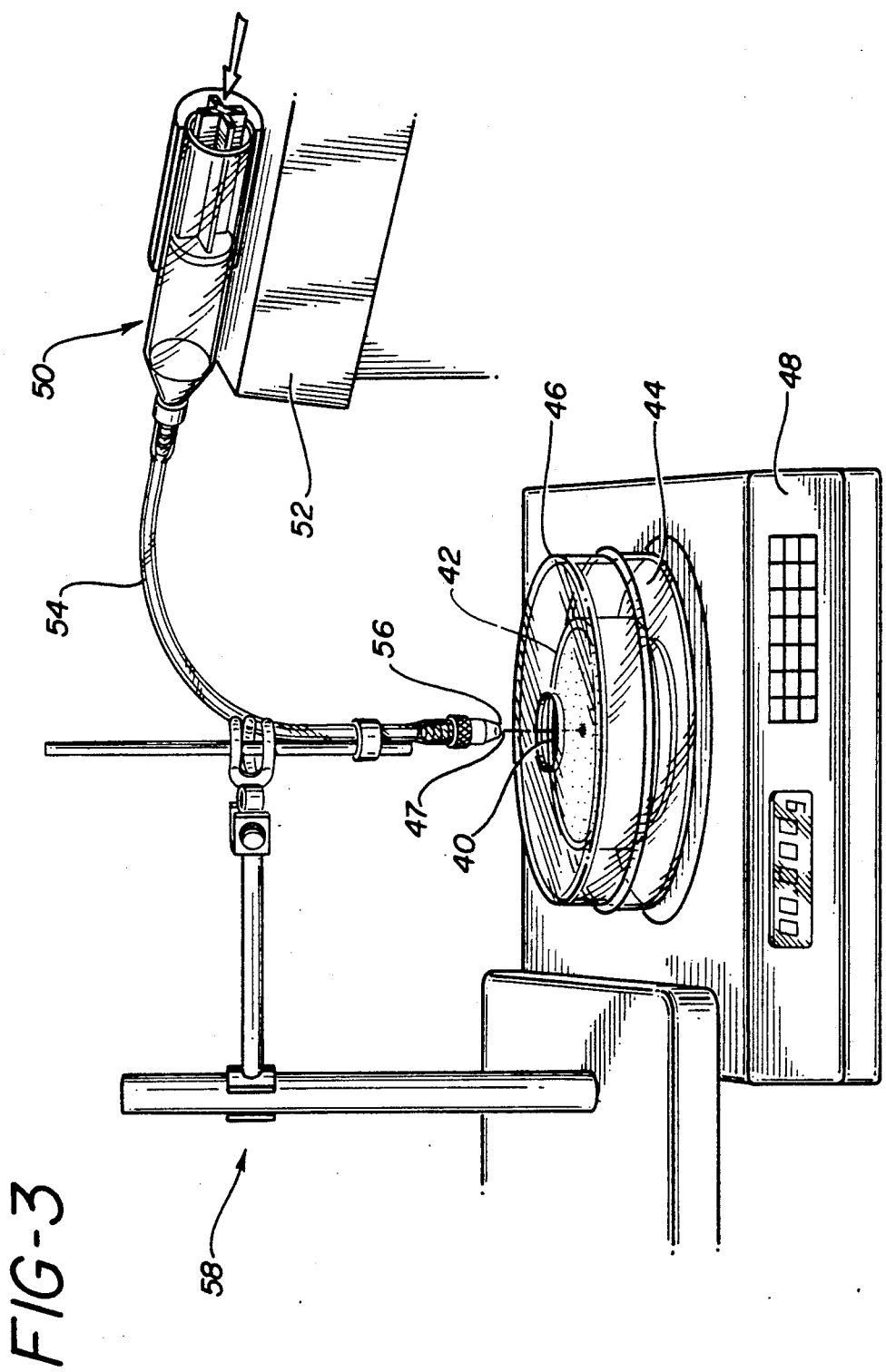
FIG. 3 is a schematic representation of a test fixture used to identify suitable materials for a composite cover.

The composite cover of the present invention, its constituent layers, and several commercially available cover materials were tested in accordance with the following procedure, which is illustrated in FIG. 3. This test procedure was designed to highlight the unidirectional fluid transmissivity properties of various composite covers and cover materials. A cover sample to be tested is cut into a 4"×4" sample size. The sample 40 is placed inside a 3" diameter sample holding hoop 42, which is tightened to maintain the sample in a taut but not stretched position across the hoop. The hoop tension was sufficient to keep the sample horizontal without sagging or wrinkling while in the hoop, and was maintained from sample to sample. The hoop with the sample is weighed on a Sartorius scale with a 0.001 gram accuracy and the weight is recorded for subsequent use. The hoop is placed in a plexiglass petri dish 44, which acts as a stand as well as a collection dish for fluid. The petri dish 44 is covered with a second petri dish 46 with a 1.5 inch hole 47 in the center. The petri dish enclosure prevents air currents from affecting the test. The petri dish enclosure containing the hoop and sample is placed on the scale 48 and the scale is tared to zero grams.

A 30 cc Becton Dickinson #5197 syringe 50 with the needle removed and the tip cut off is filled with a 1% saline solution. The syringe is mounted in a Sage Instruments syringe pump 52 Model 341A which is set for a flow rate of 3.3 cc/min. A length of Tygon tubing 54 type S-50-HL Class Vi, I.D. ⅛", O.D. ¼" is connected between the syringe and a fluid orifice 56 comprising a 16 gauge needle with a 0.08 inch opening. The fluid orifice 56 is mounted on a ring stand 58. The syringe pump is started to prime the system and fill the tubing and orifice with saline solution.

The ring stand is located so that the orifice 56 is above the hole in the petri dish. The ring stand is then adjusted to move the orifice to a position approximately one-eighth of an inch above the surface of the cover sample 40. The syringe pump is activated for twenty seconds to deposit saline solution on the sample at the 3.3 cc/min. flow rate. When the pump is shut off after twenty seconds the solution and sample are allowed to stay in place for an additional one minute and forty seconds. The total test time is thus two minutes. After the two-minute test period the total amount of solution which has been deposited on the sample surface is recorded as the reading on the scale 48.

The hoop and sample are removed from the petri dish. The reading on the scale is adjusted by the previously recorded weight of the hoop and sample to compute the weight of the solution which passed through the sample and was deposited on the surface of the bottom petri dish. The weight of the solution which is retained by the sample can then be readily calculated from the previous measurements.

The results of testing various samples in this way are shown in Table A on page 14.

In Table A, the "cover 30" refers to the preferred outer layer 30 comprising the previously described apertured film. The "insert 32" refers to the preferred liner of bicomponent fibers and rayon. The "/" indicates a composite cover of two layers. The percentages listed are an average of the percentage of deposited saline solution which passed through the samples and fell to the bottom of the petri dish 44. For each sample type, at least 20 individual samples were tested to yield the average percentage results.

TABLE A

| Sample | % of Fluid Deposited On Body-Facing Side Which Passed Through The Samples | % of Fluid Deposited On Pad-Facing Side Which Passed Through The Samples |
| --- | --- | --- |
| 1. Cover 30/ Insert 32** | 90% | 0% |
| 2. Cover 30/ Insert 32* | 0% | 0% |
| 3. Cover 30 Alone | 0% | 0% |
| 4. Insert 32 Alone | 92% | 93% |

**bonded
*not bonded

The preferred composite cover of the #1 samples is seen to exhibit the desired unidirectional fluid transmissivity characteristic. An average of 90% of the deposited solution passed through the cover and was deposited on the bottom petri dish when the fluid was deposited on the body-facing surface of the cover. When the fluid was deposited on the pad-facing side (i.e., on the insert, or liner 32), the fluid remained beaded on the sample for the full two minutes of the test and no fluid passed through the sample and fell through to the petri dish.

The #3 samples, the apertured film alone, did not pass fluid in either direction; the fluid merely spread out on the surface of the material. This demonstrates that the preferred apertured film meets the criterion of the present invention, which is that the outer layer 30 comprises hydrophobic material with sufficiently small apertures or fluid passageways so that fluid deposited on the pad-facing side does not penetrate the material.

The test of the #4 samples demonstrates that the insert 32 readily conducts fluid under the force of gravity through the liner, a liner criterion, and that there is very little lateral fluid wicking since only an average of 7-8% of the applied fluid was retained in the liner. The remainder fell through to the bottom petri dish. The #1 samples demonstrate that when the liner 32 is bonded to the upper layer 30 the wettable characteristic of the rayon fibers at the bottom of the apertures will pull the fluid through the apertures, and that the large capillary characteristic of the liner allows the fluid to continue through the liner and fall to the petri dish bottom under the force of gravity.

The test of the #2 samples demonstrate the importance of bonding the liner to the outer layer. The bonding is necessary for the wettable fibers of the liner to be intimately positioned at the bottom of the apertures of the outer layer 30 so that they will be in a position to draw the fluid through the apertures. These test results show that fluid is not drawn through the apertures to pass through the liner without the necessary bonding.

Table B on pages 17 and 18 shows the results of the same testing using commercially available cover materials alone or in combination with various liners. At least ten samples of each type were tested.

The polyethylene apertured film cover used in samples 5, 6, 10, 12, 14, and 17 was an apertured formed film topsheet treated with a non-ionic surfactant and had a basis weight of about 0.7 oz./yd.$^2$. It exhibited an average open area of 36%, an equivalent hydraulic diameter of about 0.025 inches, and an apparent thickness of about 23 mils. The surfactant treated polyethylene material is substantially hydrophobic and, as the test of the #5 samples shows, the apertures are sufficiently small so that the apertured film alone does not pass fluid. When this film is combined with a one to three mil thick liner of adhesively adhered wood pulp fibers, the composite did not exhibit the unidirectional fluid transmissivity characteristic, as seen by the test results of the #6 samples. This test result is attributable to the high absorbency and fine capillary structure of the layer of wood pulp fibers. Instead of allowing the liquid to pass through the #6 samples, the liquid was retained in the samples by the wood pulp fibers. The #12 samples comprised the same apertured film laminated to a wood pulp and meltblown polypropylene fiber liner of a thickness of about 77 mils, which is treated with a liquid polyethyoxylated ester type non-ionic surfactant.

TABLE B

| Sample | % of Fluid Passing Through From Body-Facing Side | % of Fluid Passing Through From Pad-Facing Side |
| --- | --- | --- |
| 5. Polyethylene Aper. Film | 0% | 0% |
| 6. Polyethylene Aper. Film/ Wood Pulp Fiber Liner[1] | 0% | 0% |
| 7. Spunbonded Nonwoven Polypropylene Fibers | 0% | 0% |
| 8. Spunbonded Nonwoven Polypropylene Fibers/Wood Pulp and Meltblown Polypropylene Fiber Liner* | 0% | 0% |
| 9. Spunbonded Nonwoven Polypropylene Fibers/ Insert 32* | 0% | 0% |
| 10. Polyethylene Aper. Film/ Insert 32* | 0% | 0% |
| 11. Cover 30/Wood Pulp and Meltblown Polypropylene Fiber Liner** | 0% | 0% |
| 12. Polyethylene Aper. Film/ Wood Pulp and Meltblown Polypropylene Fiber Liner** | 0% | 0% |
| 13. Cover 30/Insert 32**[2,3] | 93% | 0% |
| 14. Polyethylene Aper. Film/ Insert 32**[3] | 91% | 0% |
| 15. Spunbonded Nonwoven Polypropylene Fibers/ Insert 32** | 66% | 0% |
| 16. Cover 30/Wood Pulp and | 0% | 0% |

TABLE B-continued

| Sample | % of Fluid Passing Through From Body-Facing Side | % of Fluid Passing Through From Pad-Facing Side |
|---|---|---|
| Meltdown Polypropylene Fiber Liner* | | |
| 17. Polyethylene Aper. Film/ Wood Pulp and Meltblown Polypropylene Fiber Liner* | 0% | 0% |
| 18. Polyester apertured web/ Insert 32** | 93% | 0% |

*Not bonded
**Embossed/Laminated In Carver Press
Notes to Table B
[1]Wood pulp fibers adhered to apertured film cover with an emulsion adhesive spray.
[2]The inventive combination was laminated in the same way as test sample combinations 11, 12, and 14–15.
[3]20% of the prepared composite covers failed to pass fluid in either direction, a result attributed to variabilities inherent in the manual lamination process employed.

This liner similarly exhibits a fine capillary structure and a wettable property which causes the liner to retain liquid when the solution is applied to the body-facing side.

When this apertured film is combined with the preferred insert of the present invention but there is no lamination of the two materials, the combination fails as a composite cover as it again does not pass fluid in either direction. This is shown by the results of the test of the #10 samples, and conforms to the results of the unbonded materials of the #2 samples of Table A. However, when this apertured film is laminated to the preferred insert 32, 80% of the tested samples passed an average of 91% of the applied fluid from the body-facing side, and no fluid was passed in the tests in the reverse direction. This is shown by the results of the test of the #14 samples, which comprise composite covers satisfying the requirements of the present invention.

A spunbonded nonwoven polypropylene film cover, with a basis weight of about 0.45 oz./yd. and a thickness of about four mils was used in the preparation of samples #7–9 and #15. The test of this nonwoven cover alone showed that the material was sufficiently hydrophobic and finely apertured to satisfy the cover criteria, as shown by the results of the test of the #7 samples. The unbonded combination of this nonwoven cover and a surfactant treated wood pulp and meltblown polypropylene liner failed the test and would not pass fluid in either direction, as demonstrated by the test of the #8 samples. The unbonded combination of the nonwoven cover and the preferred insert 32 performed similarly, as the test results of the #9 samples show.

However, when the nonwoven polypropylene fiber cover was bonded to the preferred insert 32, the combination satisfied the requirements of a composite cover of the present invention as the #15 sample test results show. These samples passed an average of 66% of the fluid which was applied to the nonwoven cover, but passed no fluid in the reverse direction.

A further composite cover satisfying the criteria of the present invention is shown by the #18 samples. These samples comprise a 100% polyester apertured web which was laminated to the preferred insert 32. As the test results show, this combination exhibited excellent unidirectional fluid transmissivity properties.

The preferred apertured film cover 30 met the criteria of unidirectional fluid transmissivity when hand laminated to insert 32 as shown by the #13 samples, but failed to pass fluid in either direction when combined with or laminated to the wood pulp and meltblown polypropylene fiber liner, as the tests of the #11 and #16 samples show.

A vertical wicking test was employed to dramatize the very slight wicking characteristic of the liner used in the composite cover of the present invention. It is this characteristic which contributes to the ability of the composite cover to transmit a majority of liquid deposited on the outer layer to the absorbent core, while itself retaining an insubstantial amount of liquid, as demonstrated by the results shown in Tables A and B. This provides the absorbent product with its favorable rewet characteristics.

The liner or insert materials of Tables A and B were tested in the following manner. A dish of the 1% saline solution used in the previous test with blue dye added to provide coloration was placed on a Sartorius scale and the scale was tared to zero grams. The pool of saline solution had a depth greater than one-quarter of an inch and a surface area width greater than 2¼ inches. A liner sample of a width of 2¼ inches and a length of 6 inches was suspended at the top from a ring stand so that the bottom edge of the sample was centered over the pool of solution. The sample was suspended with the lengthwise direction oriented vertically, which direction also corresponded to the machine direction of the material. The sample was then lowered by adjustment of the ring stand until the bottom edge of the sample was submerged approximately one-quarter of an inch in the solution. The sample was observed and measured at five minute intervals following the moment the sample edge was submerged. At each time interval the distance the saline solution had wicked vertically from the surface of the pool was measured, and the weight reduction of the dish of saline solution as indicated on the scale was noted. The results of a number of these tests are shown in Table C on page 22, which show the total vertical distance travelled by the saline solution at each point in time.

The first four insert samples, In 1–In 4, were samples of the preferred insert 32 of bicomponent fibers and rayon. As the test results show, the vertical distance travelled by the solution was negligible and could not be measured.

The next five samples, In 5–In 9, were samples of one to three mil thick wood pulp fibers, the same liner material used in the #6 samples of Table B.

TABLE C

| | Height of Wicked Solution After Elapsed Time (inches) | | | | | |
|---|---|---|---|---|---|---|
| Sample No. and Type | 5 Min. | 10 Min. | 15 Min. | 20 Min. | 25 Min. | 30 Min. |
| In 1: Insert 32 | * | * | * | * | * | * |
| In 2: Insert 32 | * | * | * | * | * | * |
| In 3: Insert 32 | * | * | * | * | * | * |
| In 4: Insert 32 | * | * | * | * | * | * |
| Average of In 1–In 4: | * | * | * | * | * | * |
| In 5: Wood Pulp Fibers Adhered to Aper. Film | 1.0 | 1.0 | 1.0 | 1.25 | 1.5 | 1.5 |

TABLE C-continued

| Sample No. and Type | Height of Wicked Solution After Elapsed Time (inches) | | | | | |
|---|---|---|---|---|---|---|
| | 5 Min. | 10 Min. | 15 Min. | 20 Min. | 25 Min. | 30 Min. |
| In 6: Wood Pulp Fibers Adhered to Aper. Film | 0.5 | 1.5 | 1.5 | 1.5 | 1.5 | 1.5 |
| In 7: Wood Pulp Fibers Adhered to Aper. Film | 0.75 | 1.25 | 1.25 | 1.25 | 1.5 | 1.5 |
| In 8: Wood Pulp Fibers Adhered to Aper. Film | 1.0 | 1.0 | 1.25 | 1.25 | 1.25 | 1.25 |
| In 9: Wood Pulp Fibers Adhered to Aper. Film | 1.5 | 1.5 | 1.5 | 1.5 | 1.6 | 1.6 |
| Average of In 5–In 9: | 0.86 | 1.1 | 1.3 | 1.4 | 1.5 | 1.5 |
| In 10: Wood Pulp & Meltblown polypropylene fibers | 2.0 | 2.5 | 2.5 | 2.5 | 2.5 | 2.5 |
| In 11: Wood Pulp & Meltblown polypropylene fibers | 1.75 | 2.25 | 2.25 | 2.25 | 2.5 | 2.5 |
| In 12: Wood Pulp & Meltblown polypropylene fibers | 2.0 | 2.0 | 2.25 | 2.5 | 2.5 | 2.5 |
| In 13: Wood Pulp & Meltblown polypropylene fibers | 1.5 | 2.5 | 2.5 | 2.5 | 2.6 | 2.6 |
| Average of In 10–In 13: | 1.8 | 2.3 | 2.4 | 2.4 | 2.5 | 2.5 |

*negligible; less than 0.2"

Since this liner material itself has no integrity except that provided by being adhesively adhered to the polyethylene apertured film cover in the #6 samples, the In 5–In 9 samples comprise the cover and wood pulp fibers together. The test results are substantially unaffected by the presence of the polyethylene cover due to the hydrophobic characteristic of the cover material. The test results show a wicking distance of at least one-half inch after five minutes, and an average wicking distance for all the samples of 1.5 inches after 30 minutes. The striking but expected substantial wicking characteristic of the wood pulp fibers is consistent with the test results of the #6 samples of Table B, where the deposited liquid in those tests was retained by the samples.

Samples In 10–In 13 comprise the same wood pulp and meltblown polypropylene liner material used in samples #8, #11, #12, #16 and #17 of Table B. These samples showed an even greater wicking tendency than any of the previous samples. These samples wicked at least 1.75 inches after 5 minutes, and after 30 minutes the samples had wicked an average of 2.5 inches.

An insert sample of each type was also tested for twelve hours to determine the total vertical wicking distance after that time. These results showed that the preferred insert 32 wicked a distance of 0.2 inches after twelve hours. The wood pulp fibers adhesively adhered to the polyethylene film cover wicked a distance of 2.5 inches after twelve hours, and the wood pulp and meltblown polypropylene fiber liner wicked a distance of 4.75 inches after that time.

A liner suitable for use in a composite cover of the present invention should show a vertical wicking distance of not more than one-half inch after fifteen minutes under the preceding test conditions. Preferably, the wicking distance should not be greater than one-quarter of an inch after that time, and most preferably, the wicking distance should be negligible. After twelve hours, a suitable liner for the present inventive cover should vertically wick a distance less than 2.5 inches, and preferably less than one inch, and most preferably less than one-half inch.

Figure 4:
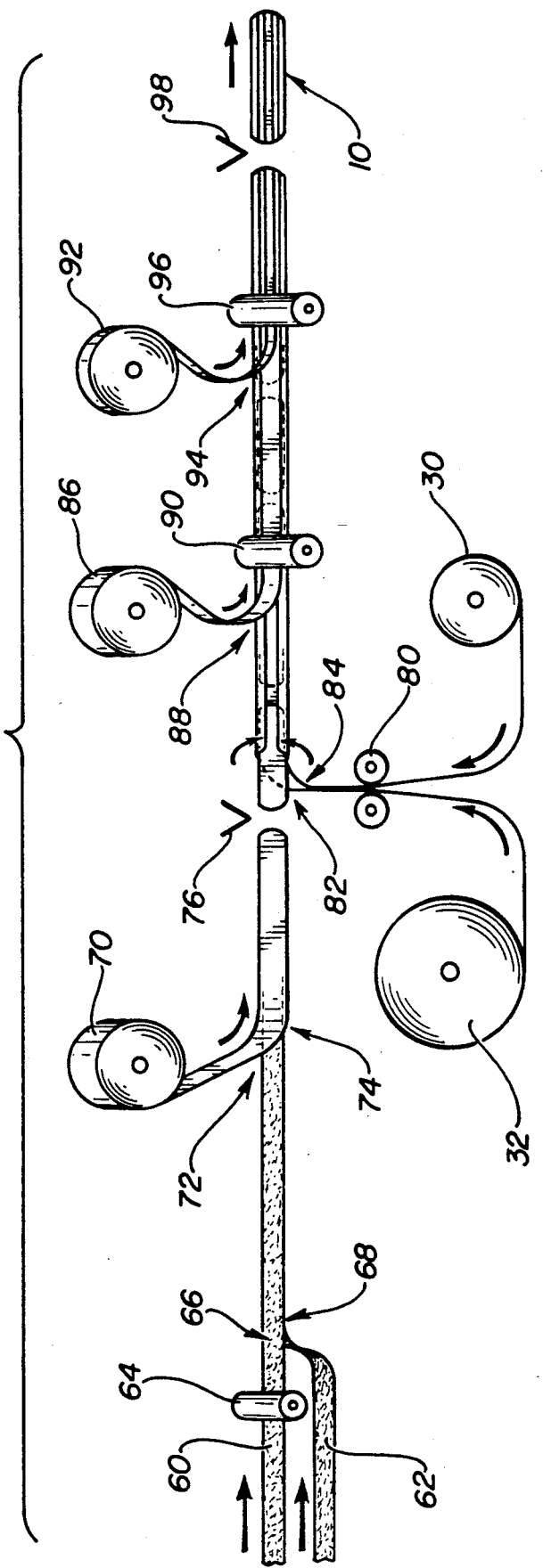
FIG. 4 is a schematic representation of a process for producing the napkin of FIG. 1.

A process for producing the preferred absorbent product 10 of FIG. 1 is schematically shown in FIG. 4. A layer of wood pulp which is homogeneously blended with superabsorbent material is shown at 60. A similar layer of low density wood pulp only is shown at 62. The layer 60 is densified by a calendar roll 64 to produce a high density layer at 66. The layers 62 and 66 are overlaid at 68, and a sheet of 0.5 mil polyethylene film for the boat 24 is unwound from a roll 70 and overlaps the superabsorbent layer 66. An emulsion adhesive is sprayed on the pad-facing side of the film, as indicated at 72. The polyethylene boat film is folded around the sides of the absorbent pad at 74, and the pad and boat are cut into individual product pads of a length of 7¼" to 8¼", depending upon the desired finished product length, by a pad knife 76.

A roll of insert material 32, prepared as described previously, is unwound together with a roll of the apertured film 30. The two materials are laminated and embossed by embossing rolls 80, which laminate the two layers together and emboss the composite cover with a snowflake pattern. The body facing surface 14 of the composite cover with its distinctive snowflake pattern is shown in full scale in FIG. 1. The embossing rolls are heated to temperatures in the range of 205° to 310° F., and apply an inversely related line pressure in the range of 1.25 to 6.25 pounds per inch width of material to the two layers to laminate and emboss the cover. An emulsion adhesive is sprayed on the pad-facing surface of the composite cover at 82, and the composite cover underlies the individual pads and is folded around the pads in a C-shaped fold at 84.

The 1.5 mil polyethylene barrier is unrolled from a roll 86, and a hot melt adhesive 88 is extruded along the edges of the barrier where the barrier overlies the sides of the cover. A crimping roll 90 seals the barrier to the sides of the cover and seals the longitudinal ends of the product. A roll of 25 lb. Akrosil release paper is unwound from a roll 92, and lines of hot melt positioning adhesive are applied at 94 to the side of the paper which faces the barrier. The release liner is adhered to the barrier by a compressing roll 96. The individual absorbent products are finally separated by a product knife 98.

Figure 5:
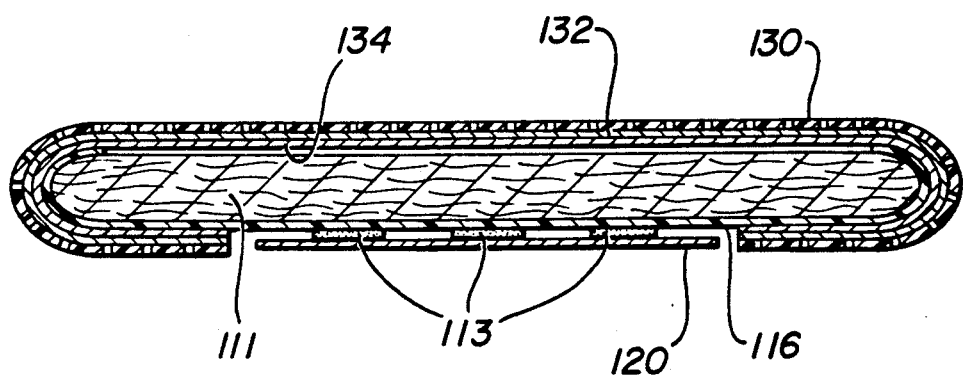
FIG. 5 is a cross-sectional view of an alternate embodiment of the present invention.

Another preferred embodiment of the present invention, which provides a highly supple absorbent product which will not soften or collapse when highly saturated, is illustrated in cross-section in FIG. 5. In outward appearance the sanitary napkins of FIG. 5 is identical to that of FIG. 1, including a like apertured film cover 130 of linear low density polyethylene and ethylene vinyl acetate and an adhesively lined barrier 116 covered by a release liner 120. The apertured film cover 130 is thermally bonded to a lofty, low density randomized fiber web 132. The web 132 comprises a homogeneous mixture of 75% of polyester fibers with a denier of 15 and a stable length of approximately 1.5 inches, available from Celanese Corp. of New York, N.Y. and 25% of bicomponent fibers with a denier of 3 and a staple length of approximately 1.5 inches, available from the American Enka Co. The fiber lengths may be varied over a range which permits them to mix thoroughly during processing. The web 132 may be prepared using a conventional Hollingsworth randomizing roll process. The preferred web 132 has a basis weight of approximately 40 grams/m$^2$ and a thickness of approximately 50 mils. The web 132 thus desirably comprises fibers which are water insensitive. As the web is saturated with fluid passing therethrough, the water insensitive fibers will not become saturated and soften or plasticize with absorbed fluid, as rayon will. The web is supple and thereby enhances the sensation of softness of the overall product with its polymeric apertured film cover. The water insensitive fibers will maintain the loft of the web by virtue of their relative inability to absorb liquid, a characteristic which is aided by the relatively high denier of the polyester fibers.

Since the web 132 is composed of essentially hydrophobic materials, it lacks the wettable characteristic necessary to pull fluids through the apertures of the cover 130. Accordingly, the web is treated with surfactant prior to bonding to give the web a slightly hydrophilic property. This may be accomplished by spraying at least the cover facing side of the web 132 with a 0.2% solution of Triton GR-5 surfactant, available from Rohm & Haas of Philadelphia, PA. Only a minimal amount of surfactant is necessary to give the web its slightly wettable characteristic. About 0.015 cc/in$^2$ to 0.025 cc/in$^2$ is used in the treatment of the web.

A single ply of tissue 134 is thermally bonded to the web on its pad facing side. The tissue acts as a carrier for the web, enclosing it between the tissue and the cover 130. The tissue is hydrophilic and aids in the transfer of fluid from the web to the absorbent pad.

The underlying absorbent pad 111 may preferably comprise wood pulp or an absorbent material comprising a peat moss base, as described in U.S. Pat. No. 4,473,440, or a combination of such materials, and may be covered with one or two plies of tissue to contain the pad material. As mentioned above, the napkin is backed by a fluid impervious barrier 116 on which are placed adhesive lines 113 for attachment of the napkin to a user's clothing.

In place of the above enumerated materials for the liner 32 or the web 132, a low density open foam could be used which exhibits the necessary capillary structure to readily pass fluid through the layer with inconsequential lateral wicking. Preferred outer layers should exhibit a thickness of one-eighth inch or less.

What is claimed is:

1. A composite cover for an absorbent product comprising:
   a first, body-facing layer of a substantially hydrophobic material containing fluid passageways therethrough, selected from the group consisting of: a coextruded, apertured film having a top surface comprising linear low density polyethylene and a bottom surface comprising ethylene vinyl acetate; a spunbonded nonwoven polypropylene; a polyester apertured web; and a polyethylene apertured film; and
   a second layer bonded to the surface of said first layer comprising porous material selected from the group consisting of: a nonwoven blend of about 75% of bicomponent fusible fibers and about 25% rayon fibers, said fusible fibers comprising a polyester core and a sheath of high density polyethylene; and a homogenous mixture of about 75% polyester fibers and about 25% bicomponent fusible fibers in the form of a lofty, low density web comprising randomized fibers, said web having been treated with surfactant;
   said fibers of said second layer being in registration with the apertures of the first layer, being minimally wettable and exhibiting a capillary gradient therethrough, with larger average capillaries opposing said first layer and relatively smaller average capillaries spaced away from the first layer, such that said composite cover exhibits unidirectional liquid flow characteristics.

2. A composite cover according to claim 1 wherein said second layer interfaces an absorbent layer into which said fluid may pass.

3. A composite cover according to claim 1 wherein said first layer comprises a coextruded, apertured film having a top surface comprising linear low density polyethylene and a bottom surface comprising ethylene vinyl acetate.

4. A composite cover according to claim 1 wherein said first layer comprises a coextruded, apertured film having a top surface comprising linear low density polyethylene and a bottom surface comprising ethylene vinyl acetate and said second layer comprises a nonwoven blend of about 75% bicomponent fusible fibers and about 25% rayon fibers, said fusible fibers comprising a polyester core and a sheath of high density polyethylene.

5. A composite cover according to claim 1, wherein said second layer comprises a homogeneous mixture of about 75% polyester fibers and about 25% of bicomponent fusible fibers in the form of a lofty, low density web comprising randomized fibers, said web having been treated with surfactant.

6. A composite cover according to claim 1 which allows a majority of fluid to pass from the body facing side to the side away from said body facing side.

7. A composite cover according to claim 1 wherein said first layer comprises spunbonded nonwoven polypropylene.

8. A composite cover according to claim 1 wherein said first layer comprises a polyester apertured web.

9. A composite cover according to claim 1, wherein said first layer comprises a polyethylene apertured film which has been treated with a non-ionic surfactant, has a basis weight of about 0.7 oz/yd$^2$, an average open area of about 36% and an equivalent hydraulic diameter of about 0.025 inches.

10. A composite cover according to claim 1 wherein said second layer contains pores of sufficient size to permit the passage of fluid without being retained in said second layer.

11. A composite cover according to claim 10 wherein said second layer comprises a homogeneous mixture of about 75% polyester fibers and about 25% bicomponent fusible fibers in the form of a lofty, low density web comprising randomized fibers, said web having been treated with surfactant.

12. A composite cover according to claim 11, wherein the basis weight of said second layer is about 0.8 oz/yd$^2$, and the thickness of said composite cover is about 0.015 inches.

13. A composite cover according to claim 10 wherein said second layer comprises a nonwoven blend of about 75% bicomponent fusible fibers and about 25% rayon fibers, said fusible fibers comprising a polyester core and a sheath of high density polyethylene.

14. A composite cover according to claim 13, wherein said apertured film has a basis weight of about 1.0 oz/yd$^2$, and has an open area of about 35 to about 45%, apertures in said apertured film having an equivalent hydraulic diameter of about 0.015 to about 0.022 inches, said bicomponent fusible fibers in said second layer have a denier of about 3.0 and staple length of about 1.5 inches and said rayon has a denier of about 1.5 and a staple length of about 1.25 inches.

15. A composite cover according to claim 14 wherein said polyester fibers have a denier of about 15.0 and a staple length of 1.5 inches and said bicomponent fusible fibers have a denier of about 3.0 and a staple length of about 1.5 inches and wherein said second layer has a basis weight of about 1.2 oz/yd$^2$ and has a treatment level of surfactant of about 0.015 cc/in$^2$ to about 0.025 cc/in$^2$.

16. A composite cover for an absorbent product comprising:
   a first, body facing layer of a substantially hydrophobic material containing fluid passageways therethrough comprising a coextruded, apertured film having a top surface comprising linear low density polyethylene and a bottom surface comprising ethylene vinyl acetate; and
   a second layer bonded to the surface of said first layer comprising porous material comprising a nonwoven blend of about 75% bicomponent fusible fibers and about 25% rayon fibers, said fusible fibers comprising a polyester core and a sheath of high density polyethylene;
   said fibers of said second layer being in registration with the apertures of the first layer, being minimally wettable and exhibiting a capillary gradient therethrough, with larger average capillaries opposing said first layer and relatively smaller average capillaries spaced away from the first layer, such that said composite cover exhibits unidirectional liquid flow characteristics.

17. A composite cover according to claim 16, wherein said apertured film has a basis weight of about 1.0 oz/yd$^2$, and has an open area of about 35 to about 45%, apertures in said apertured film having an equivalent hydraulic diameter of about 0.015 to about 0.022 inches, said bicomponent fusible fibers in said second layer have a denier of about 3.0 and staple length of about 1.5 inches and said rayon has a denier of about 1.5 and a staple length of about 1.25 inches.

18. A composite cover according to claim 16, wherein the basis weight of said second layer is about 0.8 oz/yd$^2$, and the thickness of said composite cover is about 0.015 inches.

19. A composite cover for an absorbent product comprising:
   a first, body facing layer of a substantially hydrophobic material containing fluid passageways therethrough comprising a coextruded, apertured film having a top surface comprising linear low density polyethylene and a bottom surface comprising ethylene vinyl acetate; and
   a second layer, the fibers of which are in registration with the apertures of the first layer, said second layer being bonded to the surface of said first layer comprising porous material comprising a homogeneous mixture of about 75% polyester fibers and about 25% of bicomponent fusible fibers in the form of a lofty, low density web comprising randomized fibers, said web having been treated with surfactant; said composite cover exhibiting unidirectional liquid flow characteristics.

* * * * *